United States Patent [19]

Nylen

[11] Patent Number: 4,474,690

[45] Date of Patent: Oct. 2, 1984

[54] METHOD FOR THE RECOVERY OF PEPTIDE-CONTAINING COMPOUND AND MEANS THEREFOR

[75] Inventor: Ulf Nylen, Lund, Sweden

[73] Assignee: Gambro Lundia AB, Sweden

[21] Appl. No.: 499,413

[22] Filed: Jun. 1, 1983

Related U.S. Application Data

[63] Continuation of Ser. No. 296,499, Aug. 26, 1981, abandoned.

[30] Foreign Application Priority Data

Sep. 2, 1980 [SE] Sweden .................. 80 06102

[51] Int. Cl.³ .................. C07G 7/02; C07G 7/00
[52] U.S. Cl. .................. 260/112 R; 210/651; 525/54.21
[58] Field of Search .................. 260/112 R; 210/651; 525/54.21

[56] References Cited

U.S. PATENT DOCUMENTS

| | | | |
|---|---|---|---|
| 3,502,545 | 3/1970 | Westman et al. | 260/112 R |
| 3,687,928 | 8/1972 | Brouwer et al. | 260/112 R |
| 3,867,501 | 4/1975 | Hanushewsky | 260/112 R |
| 4,066,505 | 1/1978 | Schneider | 260/112 R |
| 4,402,874 | 9/1983 | Johnson et al. | 260/112 R |

Primary Examiner—Maurice J. Welsh
Assistant Examiner—Nathan M. Nutter
Attorney, Agent, or Firm—Lerner, David, Littenberg, Krumholz & Mentlik

[57] ABSTRACT

A method is disclosed for the recovery of a peptide-containing compound from a solution by the use of a ligand attached to a carrier which ligand is capable by biospecific affinity of fixing onto the peptide-containing compound. The carrier which, for example, may be a soluble macromolecule, e.g., cellulose or dextran, with ligand attached thereto, is utilized in dissolved form. The choice of ligand is determined by the type of peptide-containing compound for which it is to be used. Example of ligands which may be used are immunoglobulins, Fc-receptors, certain surface receptors from bacteria, e.g., protein A from *S. aureus*, co-factors and certain sugar-containing proteins. The ligand may be attached to the carrier by bonds of a covalent character, which may be achieved by periodate activation and subsequent coupling or by diimidazole coupling.

18 Claims, 2 Drawing Figures

Fig. 2

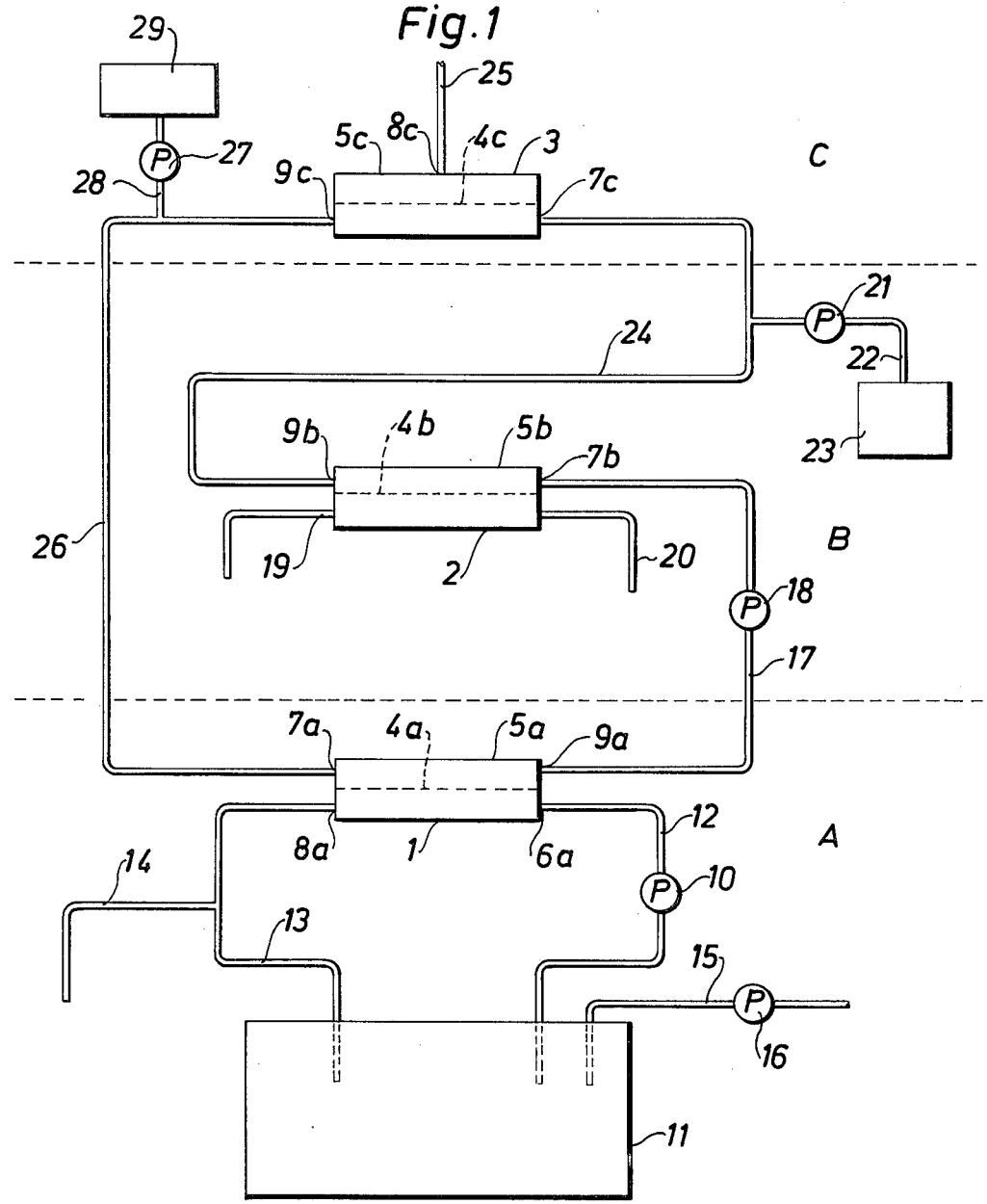
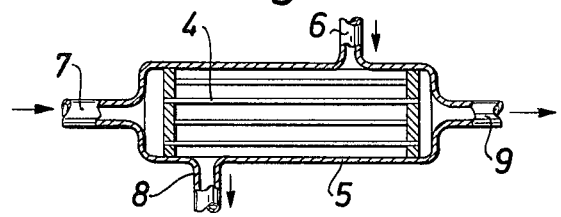

METHOD FOR THE RECOVERY OF PEPTIDE-CONTAINING COMPOUND AND MEANS THEREFOR

This is a continuation, of application Ser. No. 296,499 filed Aug. 26, 1981, now abandoned.

FIELD OF THE INVENTION

The present invention relates to a method for the recovery of a peptide-containing compound from a solution which contains the peptide-containing compound, possibly together with other compounds of a contaminant character. The invention relates moreover to a means for the realization of the above-mentioned method.

BACKGROUND OF THE INVENTION

Methods and means for separating a peptide-containing compound are known. For example, U.S. Pat. No. 3,850,798 discloses a process which employs a ligand attached to a carrier which is a solid substance and which is insoluble in the solution from which the peptide-containing compound is to be recovered. Thus, for example, the carrier with the ligand attached to it may be present in the form of particles which have been collected as a mass in a column through which the solution is made to flow in order to achieve contact between the ligand and the peptide-containing compound so as to form a complex of the carrier, the ligand and the peptide-containing compound.

SUMMARY OF THE INVENTION

It has now been found that in accordance with the present invention an improvement in the above-mentioned known method can be achieved by employing a carrier with ligand attached to it in dissolved form, instead of the solid form which is used in accordance with the U.S. patent. It has been found, inter alia, that, with such a complex-forming means in dissolved form, a more uniform and better distribution of the means throughout the solution is achieved, as a result of which a more effective contact between the peptide-containing compound and the attached ligand and therefore more effective formation of the complex is provided. The diffusion length between these two substances, for example, will be shorter than if the means is present in solid form. Furthermore, any steric and/or mechanical hindrances for contact between the two substances will be fewer. This likewise contributes to an increase in the effectiveness of the present method, because as a result the peptide-containing compound can be fixed onto the ligand, and later liberated from the same, more readily. It is a further advantage that the method in accordance with the invention can be carried out in a homogeneous phase, that is to say the liquid phase, which helps to create better prerequisites for the prevention of flow problems or similar interruptions of the process and to provide improved conditions for a continuous process.

The method in accordance with the invention is applicable to the recovery of a protein in free form. It can be utilized, for example, in continuous industrial processes, where the recovery of the protein takes place, in that a solution containing the protein can be brought into contact with an immunoglobulin attached to a carrier so as to fix the protein by biospecific affinity to the immunoglobulin, and where the protein so fixed is afterwards separated from the immunoglobulin in order to obtain the protein in free form. Protein A, in particular, can be recovered by bringing the solution into contact with IgG which has been attached to soluble dextran.

DETAILED DESCRIPTION OF THE INVENTION

In accordance with the present invention, a method is thus provided for the recovery of a peptide-containing compound, possibly together with other compounds of a contaminant character. This method comprises the steps or stages of: bringing a solution including the peptide-containing compound into contact with a ligand attached to a carrier, said ligand and attached carrier being in dissolved form and said ligand being capable by biospecific affinity of fixing onto the peptide-containing compound so as to form a soluble complex of said carrier, ligand and peptide-containing compound; subsequently liberating the peptide-containing compound from the complex formed; and separating and recovering the peptide-containing compound liberated.

Preferably, the solution which contains the peptide-containing compound is miscible with the solution containing the ligand with attached carrier. More preferably, both are aqueous solutions.

In a preferred embodiment the solution containing the peptide-containing compounds is first filtered, prior to contact with the ligand attached to the carrier. This can be done through a membrane filter so as to remove any compounds of a contaminant character, e.g., contaminants with molecular weights above a predetermined limit.

The filter may be constituted, for example, of hollow fibers with the wall pores adapted so that contaminations of molecular weights above a certain limit are retained, while other compounds (including the peptide-containing compound) of molecular weights below such limit may pass freely through these pores into the axial cavities of the fibers. The hollow fibers can be enclosed within an outer jacket with inlets and outlets in the same manner as in a so-called artificial kidney of the hollow fiber type. The solution to be filtered is made to flow in the space outside the fibers, while the solution containing the dissolved carrier with attached ligand is made to flow through the axial cavities of the fibers. The pores of the fiber walls naturally should be adapted so that the dissolved carrier with ligand attached is not allowed to pass through the fiber walls.

Examples of membrane filters which fulfill these conditions and which can be used in accordance with the invention are hollow fibers with a cut-off around $5 \times 10^5$ Dalton (D). Membrane filters in forms other than the hollow fiber may also be used, for example, plane or helical membranes.

For the further separation of any compounds of a contaminant type present, the solution which contains the complex formed of carrier, ligand and peptide-containing compound can also be subjected to a membrane filtration using a membrane filter of the same type as that described above, but with a cut-off which is preferably somewhat higher than the previously discussed one. Examples of such membrane filters may be hollow fibers with a cut-off around $10^6$D. However, this cut-off must be such that the complex formed is retained in the solution.

To increase the degree of separation of these compounds, it may be appropriate to use several membrane filters coupled in series, the solution being made to flow in turn through these filters with successively growing separation of the compounds. To compensate for the loss in liquid which occurs as a result and at the same time to maintain an appropriate pH in the remaining solution, a weak buffer solution can be added to the remaining solution in connection with this series filtration. The term appropriate pH here means a pH which is such that the bond between the ligand and the peptide-containing compound is not broken. Examples of such appropriate pH values may be between 6 and 9.

To liberate the peptide-containing compound from the complex formed, an acid can be added which alters the pH of the solution and thereby breaks the bond. Alternatively, this bond may be broken by adding a little salt solution which increases the ionic strength of the solution.

The peptide-containing compound thus liberated can then be separated and recovered by appropriate means, such as by a further membrane filtration. In such separation and recovery, a membrane filter can be employed which is adapted so that it lets through the peptide-containing compound liberated but retains the carrier with the ligand attached to it. This membrane filter too may be of the same type as those mentioned earlier. A suitable cut-off is between $5 \times 10^5$ and $10^6$D.

To restore the pH of the solution after separation and recovery of the peptide-containing compound, a base can be added which raises the pH of the solution to the neutral point. The solution so adjusted, containing the carrier with ligand attached, may then be used anew.

The complex forming means for the realization of the method in accordance with the invention comprises a ligand which is attached to a carrier and which is capable by biospecific affinity of fixing onto a peptide-containing compound so as to form a complex of the said carrier, ligand and peptide-containing compound, wherein the carrier with the ligand attached to it is soluble in a liquid phase, preferably in an aqueous solution, which contains the peptide-containing compound which is to be recovered.

The choice of ligand is determined by the type of peptide-containing compound which is to be recovered, inasmuch as these two substances must be able to fix onto one another by biospecific affinity. Examples of ligands usable in accordance with the invention are immunoglobulins, Fc-receptors, certain surface receptors from bacteria with affinity for the Fc-part (e.g., *S. aureus* protein A) cofactors, and certain sugar-containing proteins.

Examples of peptide-containing compounds, which can be recovered by the method in accordance with the invention and which consequently can by biospecific affinity fix onto, for example, anyone of the above-listed usable ligands, include antigens, immunoglobulins, enzymes and lecithins.

Among examples of carriers in accordance with the invention may be mentioned soluble macromolecules with molecular weights above the molecular weight of the peptide-containing compound which is to be recovered. Examples of such macromolecules may be soluble types of sugars, in particular cellulose or dextran. Another example would be a soluble polyacrylamide.

The ligand is attached to the carrier preferably by bonds of a covalent character. Such bonds can be achieved, for example, by periodate activation of the carrier with subsequent coupling to the ligand. The bonds may also be achieved by diimidazole coupling. Various other procedures for achieving such attachments between a carrier and a ligand are well-documented in the available literature on the subject and do not need to be discussed in detail here.

BRIEF DESCRIPTION OF THE DRAWINGS

The invention will be more clearly understood by reference to the accompanying drawings in which:

FIG. 1 shows a schematic representation of how the steps of the method in accordance with the present invention can be integrated to a continuous process; and FIG. 2 shows a partial cross-section of a suitable practical embodiment of a membrane filter for use in the process illustrated in FIG. 1.

DETAILED DESCRIPTION OF THE DRAWINGS

In FIG. 1 letters A, B and C are intended to represent schematically the separate stages or steps in the method according to the invention. Thus letter A designates the contact stage, B designates the stage of the liberation of the peptide-containing compounds and C designates the separation and recovery stage.

In everyone of these three stages preferably a membrane filter 1, 2 and 3 respectively is used, with a pore-size cut-off depending upon the compound which is to be recovered. A suitable embodiment of such a filter is shown schematically in FIG. 2. Here the filter is designed as a so-called artificial kidney of the hollow-fiber type with hollow fibers 4 enclosed within an outer jacket 5 with inlets 6, 7 and corresponding outlets 8,9. For a more detailed description of such an artificial kidney, reference is made, for example, to U.S. Pat. No. 3,228,877, the disclosure of which is incorporated herein by reference. For corresponding parts of the membrane filters 1, 2 and 3 in FIG. 1, the same reference numerals are used here as in FIG. 2, but with the addition of the letters a, b and c, respectively.

STAGE A

The first solution containing the peptide-containing compound to be recovered is pumped with the help of a pump 10 from a culture tank 11 to the membrane filter 1 via a line 12 and an inlet 6a. The culture tank 11 contains bacteria which can produce the peptide-containing compound. Inside the membrane filter 1 the solution, which is conducted through the space between the hollow fibers 4 and the jacket 5a, will be filtered through the pores in the fiber walls owing to the pressure difference which is maintained between this space and the inner cavities of the fibers. The hollow fibers 4a are adapted so that contaminations of molecular weights above a certain defined limit, e.g., $5 \times 10^5$D, are retained in the solution outside the fibers, while compounds (including the peptide-containing compound which is to be recovered) with molecular weights below this limit pass through the wall pores of the fibers into the inner cavity of the fibers to make contact with the solution flowing through this cavity and containing the carrier with ligand attached thereto. The retained second solution outside the fibers is conducted out of the membrane filter 1 through the outlet 8a and is returned to the culture tank 11 via a line 13 after drawing off the bacteria slop through a withdrawal line 14. Fresh culture medium is supplied via a line 15 with the help of a pump 16.

STAGE B

From the stage A the second solution with the complex of carrier, ligand and peptide-containing compound formed is pumped with the help of a pump 18 from the membrane filter 1 to the membrane filter 2 via a line 17 connected to the outlet 9a on the membrane filter 1 and the inlet 7b on the membrane filter 2. Inside the membrane filter 2, such second solution is filtered through the pores in the hollow fibers 4b so as to separate any contaminations which may have remained in the solution. The hollow fibers 4b are adapted so that contaminations of molecular weights below a certain defined limit, e.g., $10^6$D, pass through the wall pores out of the inner cavity of the fibers, while compounds (including the complex formed) with molecular weights above this limit are retained in the solution inside the cavity of the fibers.

To compensate for the loss in liquid, which occurs owing to the filtration in the membrane filter 2, and in order to maintain an appropriate pH in the remaining solution, a weak buffer solution is added appropriately through a line 19 in connection with the filtration. The filtrate formed in discharged via a line 20.

After this filtration of the second solution with the complex formed, a means for altering the pH is added so as to break the bond between the ligand and the peptide-containing compound so as to liberate the peptide-containing compound from the complex. For example, an acid can be added to lower the pH. This addition may be done, for example, with the help of a pump 21 in a line 22 connected to a source 23 of acid and a line 24. The line 24 is connected to the outlet 9b on the membrane filter 2 and the inlet 7c on the membrane filter 3 and is arranged so that it conducts solution from the membrane filter 2 to the membrane filter 3.

STAGE C

The solution with the peptide-containing compound thus freed is conducted into the membrane filter 3, into the cavities of the hollow fibers 4c, via the said inlet 7c, for the separation and recovery of the liberated peptide-containing compound via a line 25 in connection with the outlet 8c on the membrane filter 3. The hollow fibers 4c are adapted so that compounds (including the peptide-containing compound liberated) with molecular weights below a defined limit, e.g., $5 \times 10^5$ or $10^6$D, pass through the wall pores of the fibers 4c, while compounds (including the carrier and the ligand attached to it) with molecular weights above the same limit are retained in the solution inside the cavity of the fibers.

From the membrane filter 3, the solution with the carrier and the ligand attached thereto is returned to the membrane filter 1 via a line 26 in connection with the outlet 9c on the membrane filter 3 and the inlet 7a on the membrane filter 1 for reuse in stage A.

To restore the pH of the solution, a base (possible together with carrier/ligand) can be added with the help of a pump 27 in a line 28 connected to a source 29 of base and the line 26.

The following examples are intended to illustrate, but not to limit, the present invention.

EXAMPLE 1

This example illustrates the recovery of protein A with dextran as the carrier for the ligand which is constituted of a immunoglobulin.

Materials:

IgG, purified by protein A affinity chromatography on solid phase, attached to Dextran-2000 (M=$2 \times 10^6$D) (4.2 IgG per molecule dextran).

Protein A labelled by $I^{125}$.

IgG from affinity chromatography on solid phase, labelled by $I^{131}$.

Citric acid (pA), potassium dihydrogen phosphate (pA), dipotassium hydrogen phosphate (pA).

Membrane filter in the form of hollow fibers with a specified cut-off of $10^6$D.

Experiment I

To 500 ml of 0.1M phosphate buffer at pH 7.3 are added 100 ml of a solution containing the IgG attached to Dextran-2000. Radioactive protein A is added in deficit. The solution is mixed for 1 minute and subsequently pumped with a flow rate of approximately 150 ml/min through the cavities in the membrane fibers and back to the mixing vessel. The filtrate formed fills successively the space outside the fibers. For the sake of clarity, it should be mentioned that the hollow fibers are enclosed within an outer jacket in the same manner as, for example, in a so-called artificial kidney of the hollow-fiber type. The filtrate is drawn off at the top, at the rate as it is formed. A pressure difference of 10 to 40 cm $H_2O$ is maintained, at which dialyzate is formed at a rate of approximately 40 ml/min. Samples are taken at different stages of the concentration process from the dialyzate, as well as from the solution used. The solution is diluted to 2 liters and the concentration process continues during the sample taking.

Blue dextran of a molecular weight $2 \times 10^6$D had been tested earlier and was found to pass the membrane so that the concentration in the filtrate will be 2.5% of the concentration in the solution used under similar conditions.

The measurement of the respective samples was carried out in a gamma counter: (spA-$I^{125}$)

The result of the measurements is shown in Table I below:

TABLE I

| Sample[b] No. | Protein A measured value, cpm/2 ml | | % Protein A which has passed through the membrane in relation to the liquid volume |
|---|---|---|---|
| | Main Solution | Filtrate | |
| 1 | 31,000 | 4,200 | 13.5 |
| 2 | 47,000 | 4,700 | 10.0 |
| 3[a] | 31,092 | 2,854 | 9.2 |
| 4 | 41,102 | 2,879 | 7.0 |

[a]dilution of the remaining solution
[b]Samples No. 1, 2, 3 and 4 were drawn after the formation of 100, 400, 800 and 1,300 ml filtrate, respectively.

Owing to the somewhat long standstill in connection with the start of the experiment (sample 1), a little too much protein A had passed through the membrane initially. The figure of 10%, however, may be regarded as fairly adequate. The end value of 7% (sample 4) is probably due to the fact that the quantity of free IgG has diminished in the main solution owing to the dialysis process.

Since only 2.5% dextran should have passed the membrane, if all the protein A added has become attached to the dextran, there is good reason for assuming that 7.5% derive from protein A attached to free IgG. Since protein A attached to IgG in free form passes almost unhindered through the membrane (retention about 20%; based on the result of experiment II), it thus appears from this experiment that the binding capacity for free IgG constitutes less than 10% of the binding capacity for dextran-attached IgG.

Dialysate and main solution are put together and the pH is adjusted to 3 (measured with pH paper) by means of 1M citric acid. The solution is mixed and a new concentration process is started. Volume about or equal to 2.3 l.

The following measuring results were obtained:

TABLE II

| Sample[a] No. | Protein A measured value, cpm/2 ml | | % Protein A liberated |
|---|---|---|---|
| | Main solution | Dialyzate | |
| 5 | 14,800 | 12,380 | 83.6 |
| 6 | 15,900 | 13,410 | 84.3 |
| 7 | 18,110 | 14,400 | 79.5 |

[a]Samples No. 5, 6 and 7 taken after formation of 400, 1000 and 1400 ml dialyzate, respectively.

Table III shows that the protein A is liberated and can readily be filtered out at pH=3.

Experiment II

The procedure is the same as in Experiment I, but beside radioactive protein A $I^{125}$, which is added last, 10 mg IgG labelled by $I^{131}$ are also added.

The solution is immediately diluted to 2 liters and mixed for 1 minute, pH=7.3.

To determine the interference between $I^{125}$ and $I^{131}$, a measurement is carried out first on the pure preparation with the two "windows" which will also be used later, "window" A (0-40) and "window" B (50-500). The following measured values were obtained.

TABLE III

| Window | Measured value, cpm/2 ml | |
|---|---|---|
| | $I^{125}$ | $I^{131}$ |
| A | 16,350 | 308 |
| B | 40 | 2,325 |

Thus in window B, within the accuracy of measurement, exclusively $I^{131}$ was measured, while the measuring result in window A is a sum of $I^{131}$ and $I^{125}$. The measuring results given below in Table IV have been compensated so that measured values are indicated for each isotope separately.

TABLE IV

| Sample[a] No. | Protein A measured value, cpm/2 ml | | IgG measured value, cpm/2 ml | |
|---|---|---|---|---|
| | main solution | dialyzate | main solution | dialyzate |
| 8 | 15,018 | 5974 (25.1%) | 17,904 | 11,778 (66%) |
| 9 | 17,868 | 7250 (41%) | 17,928 | 16,067 (89%) |
| 10 | 23,558 | 7570 (32%) | 19,600 | 17,328 (88%) |
| 11 | 33,823 | 7713 (22%) | 20,500 | 17,304 (84%) |

[a]Samples No. 8, 9, 10 and 11 taken after formation of 200, 800, 1200 and 1600 ml dialyzate, respectively.

The percent figures in parentheses in the above Table IV indicate the measure of protein A and the quantity of IgG, respectively, which have passed through the membrane. Table IV makes evident, therefore, that free IgG easily passes the membrane, and also that free IgG with attached protein A passes readily. The experiment equally shows that 10 mg IgG which have been added together with the IgG already present, constitute a good 30% of the binding capacity, that is to say the 10 mg IgG which have been added constitute approximately 20% of the bonding capacity and the dextran-attached IgG 70%. Approximately 50 mg IgG or a protein A binding capacity of approximately 15 g exists therefore in added dextran.

The experiment also makes evident that this short filtration has led to the "contamination" IgG being reduced to approximately 50% in relation to the protein A.

The pH is adjusted to 3 (measured with pH paper) by means of 1M citric acid (volume approximately 2.3 l) after the dialyzate found earlier has been mixed again with the main solution. The solution is concentrated as before. The following result was obtained:

TABLE V

| Sample[a] No. | Protein A measured value, cpm/2 ml | | IgG measured value, cpm/2 ml | |
|---|---|---|---|---|
| | main solution | dialyzate | main solution | dialyzate |
| 12 | 11,906 | 11,863 (100%) | 12,933 | 682 (52%) |
| 13 | 11,978 | 10,507 (88%) | 12,867 | 7055 (55%) |
| 14 | 13,106 | 9,602 (73%) | 14,828 | 6682 (45%) |
| 15 | 16,719 | 11,424 (69%) | 20,730 | 7252 (35%) |

[a]Sample Nos. 12, 13, 14 and 15 taken after formation of 400, 800, 1200 and 1800 ml dialyzate, respectively.

The percent figures in parentheses in Table V indicate the measure of the quantity of protein A and IgG, respectively, which pass through the membrane. Table V makes evident, therefore, that protein A passes well through the membrane, while IgG for some reason is strongly retarded at this pH, as distinguished from its behavior at pH=7.3 (Table IV). Presumably, this is due to the pH having become somewhat too low, giving rise to (aggregation) denaturation of IgG, which means then that the protein cannot be dialyzed. Such a denaturation (unspecified aggregation) may even be thought to affect the solubility of protein A through occlusion.

The above-mentioned experiments suggest that this system can be used for the purification of protein A. To obtain satisfactory affinity-chromatographic purification with the membrane and carrier used in the example, it is necessary, however, that the filtration and concentration stages are repeated a number of times. In an industrial process, it would be necessary, therefore, in order to simplify and to accelerate the process, if the above-mentioned membrane is used, to employ a somewhat larger carrier molecular, e.g., dextran or cellulose of a molecular weight around $5 \times 10^6$ D. Alternatively, a membrane with somewhat smaller pores can be used, that is to say a membrane which has a cut-off (approximately 90% retention) of $7 \times 10^5$ D, instead of that used of approximately $10^6$ D.

Example II

This example illustrates the coupling of IgG to dextran according to the method with periodate activation.

Materials:

Dextran T2000 (Pharmacia Fine Chemicals), sodium metaperiodate (Merck) and sodium borohydride (Merck).

2 grams of dextran T2000 are dissolved in 50 ml of distilled water. 10 ml of newly prepared 0.1M sodium periodate solution (in water) are added and the whole mixture is allowed to stand with stirring for 20 minutes at room temperature. Subsequently, the mixture is dialyzed against 1.0 mM sodium acetate buffer, pH 4.4, for 6 hours at room temperature with change of buffer every hour. The pH in the mixture is increased to 9.3 by addition of 0.2M sodium carbonate buffer, pH 9.5. 310 ml of IgG solution (obtained by dialysis against 0.01M carbonate buffer, pH 9.5, during 6 hours at room temperature and subsequent concentration and storage in the cold) are added, and the whole mixture is stirred for 2 hours. The IgG solution had also been dialyzed against 0.01M sodium carbonate buffer, pH 0.3, during 2 hours. 66 mg of sodium borohydride dissolved in 8 ml of distilled water are added. The mixture is allowed to stand in the refrigerated chest for 2 hours and is filtered subsequently through a membrane with a cut-off of $1 \times 10^6$D. A calculation of the yield showed that 4.2 molecules of IgG had been coupled per molecule of dextran T2000. The overall yield was as high as approximately 75%.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A method employing a homogeneous phase for the recovery of a peptide-containing compound, said method comprising the steps of (a) bringing said peptide-containing compound into contact with a solution containing a ligand attached to a carrier, said ligand and attached carrier being in soluble form and said ligand being capable by biospecific affinity of fixing onto the peptide-containing compound so as to form a homogeneous phase of a soluble complex of said carrier, said ligand and said peptide-containing compound in said solution; (b) separating contaminations having a molecular weight lower than the molecular weight of said soluble complex from said homogeneous phase containing said soluble complex without separating said soluble complex from said homogeneous phase; (c) liberating said peptide-containing compound from said soluble complex in said homogeneous phase to reform said ligand with attached carrier and said peptide-containing compound in said homoegeneous phase; and (d) separating and recovering said liberated peptide-containing compound from said homogeneous phase.

2. A method employing a homogeneous phase for the recovery of a peptide-containing compound from a solution containing said peptide-containing compound, said method comprising the steps of (a) subjecting said solution to a first membrane filtration so as to remove contaminants with molecular weights above a predetermined limit greater than the molecular weight of the peptide-containing compound to provide a first filtrate solution containing said peptide-containing compound; (b) bringing said first filtrate solution into contact with a ligand attached to a carrier, said ligand and attached carrier being in soluble form and said ligand being capable by biospecific affinity of fixing onto the peptide-containing compound so as to form a homogeneous phase of a soluble complex of said carrier, said ligand and said peptide-containing compound in said first filtrate solution; (c) subjecting the first filtrate solution containing said soluble complex to a second membrane filtration so as to remove contaminants from said first filtrate solution with molecular weights below a predetermined limit lower than the molecular weight of said soluble complex to provide a second filtered solution; (d) liberating said peptide-containing compound from the soluble complex in said second filtered solution to reform said ligand with attached carrier and said peptide-containing compound in said second filtered solution; and (e) subjecting said second filtered solution containing the liberated peptide-containing compound and the ligand with attached carrier to a third membrane filtration so as to filter the peptide-containing compound from the ligand with attached carrier.

3. A method according to claim 2, wherein said predetermined limit is $5 \times 10^5$ Dalton.

4. A method according to claim 2, wherein said peptide-containing compound is liberated through an alteration of the pH.

5. A method according to claim 4, wherein said alteration of pH is accomplished through addition of an acid so as to break the bond between the ligand and the peptide-containing compound.

6. A method according to claim 2, wherein said peptide-containing compound is liberated through the addition of a salt solution to increase the ionic strength of the solution.

7. A method according to claim 2, wherein said third membrane filtration is adapted so that it lets through the peptide-containing compound but retains the carrier with the ligand attached to it.

8. A method according to claim 7, wherein said third membrane filtration has a cut-off between $5 \times 10^5$ and $10^6$ Dalton.

9. A method according to claim 7, wherein the carrier and the ligand attached to it from step (e) is re-used in step (b).

10. A method according to claim 9, wherein, prior to said re-use, the pH of the solution with the carrier and the ligand attached to it is restored.

11. A method according to claim 2, wherein a weak buffer solution is added in connection with said step (c) so as to maintain the pH of said solution containing the complex at about the neutral point.

12. A process according to claim 2, wherein said ligand is selected from the group consisting of immunoglobulins, Fc-receptors, surface receptors from bacteria with affinity for the Fc-part co-factors, and sugar-containing proteins.

13. A process according to claim 2, wherein said ligand is protein A from *S. aureus*.

14. A process according to claim 2, wherein said ligand is attached to said carrier by bonds of a covalent character.

15. A process according to claim 2, wherein said carrier is a soluble macromolecule of a molecular weight above the molecular weight of the peptide-containing compound to be recovered.

16. A process according to claim 15, wherein said macromolecule is a soluble sugar.

17. A process according to claim 16, wherein said soluble sugar is selected from the group consisting of cellulose and dextran.

18. A process according to claim 15, wherein said macromolecule is a polyacrylamide.

* * * * *

UNITED STATES PATENT AND TRADEMARK OFFICE
CERTIFICATE OF CORRECTION

PATENT NO. : 4,474,690
DATED : October 2, 1984
INVENTOR(S) : Ulf Nylen

It is certified that error appears in the above-identified patent and that said Letters Patent is hereby corrected as shown below:

Column 8, Table V, under column entitled dialyzate, change "682" to --6828--.

Signed and Sealed this

Fourteenth Day of May 1985

[SEAL]

Attest:

DONALD J. QUIGG

Attesting Officer

Acting Commissioner of Patents and Trademarks